United States Patent [19]

Rumph et al.

[11] 4,237,876

[45] Dec. 9, 1980

[54] ANTI-RAPE DEVICE

[75] Inventors: Joel D. Rumph, 8875 Armaria Ct., Elk Grove, Calif. 95624; Lynda K. Warren, Elk Grove, Calif.

[73] Assignee: Joel Darren Rumph, Elk Grove, Calif.

[21] Appl. No.: 85,497

[22] Filed: Oct. 17, 1979

[51] Int. Cl.³ .............................................. A61B 19/00
[52] U.S. Cl. ............................ 128/138 R; 128/218 F
[58] Field of Search ............... 128/132 R, 138, 218 F

[56] References Cited

U.S. PATENT DOCUMENTS

| | | | |
|---|---|---|---|
| 3,563,098 | 2/1971 | Gley | 128/218 F |
| 3,841,328 | 10/1974 | Jensen | 128/218 F |
| 4,016,875 | 4/1977 | Levesque | 128/138 R |
| 4,030,490 | 6/1977 | Vogel | 128/138 R |
| 4,148,310 | 4/1979 | Coetzee | 128/138 R |
| 4,167,183 | 9/1979 | Barlow | 128/138 R |

*Primary Examiner*—Lawrence W. Trapp
*Attorney, Agent, or Firm*—Donald E. Nist

[57] ABSTRACT

An anti-rape device having a hollow housing adapted to be worn within a human vagina. The housing has a front opening and contains a hypodermic syringe having a volume of rape-deterring fluid and a needle facing and aligned with the front opening. Actuator means in the housing are provided which include housing means such as a spring to force the needle through the front opening and inject the fluid, cocking means to cock the device into a position which totally shields the needle within the housing, and prevents action of the spring, and trigger means which automatically releases the cocking means, upon forceful penis penetration of a vagina containing the device, to permit the spring to protrude the needle and inject the fluid into the penis. Preferably, the fluid is a quick-acting, safe narcotic such as scopolamine, or the like to render the rapist unconscious.

10 Claims, 6 Drawing Figures

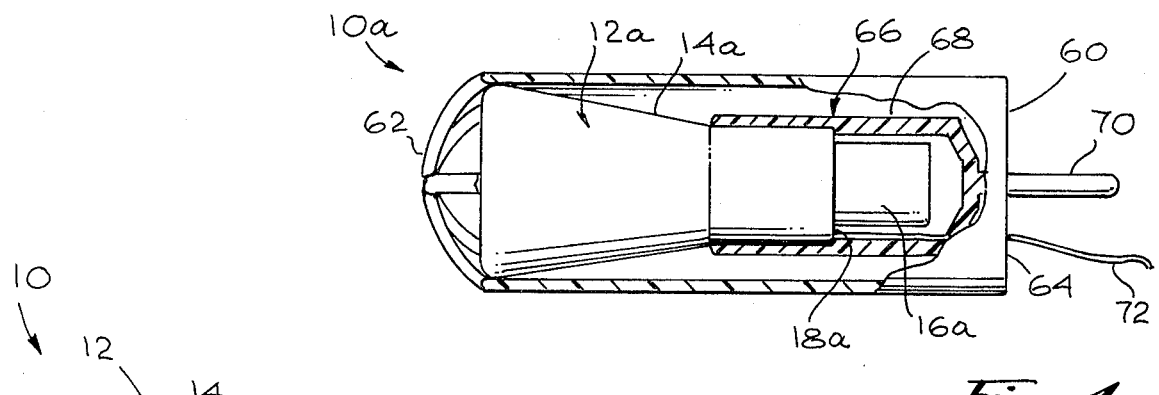
Fig. 4
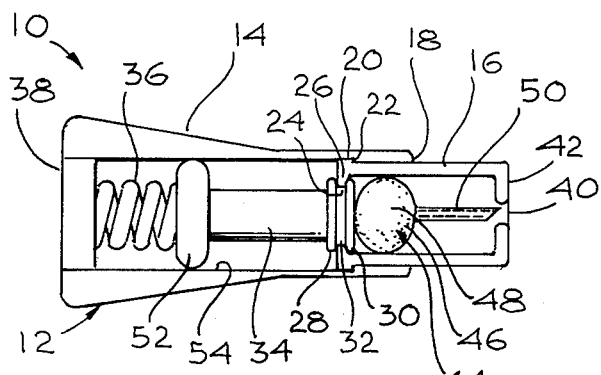
Fig. 1
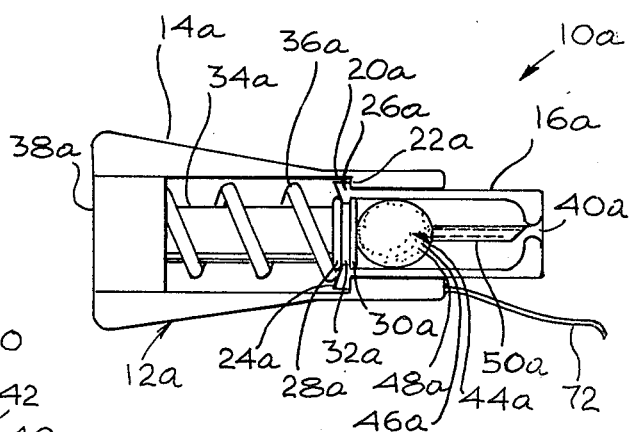
Fig. 5
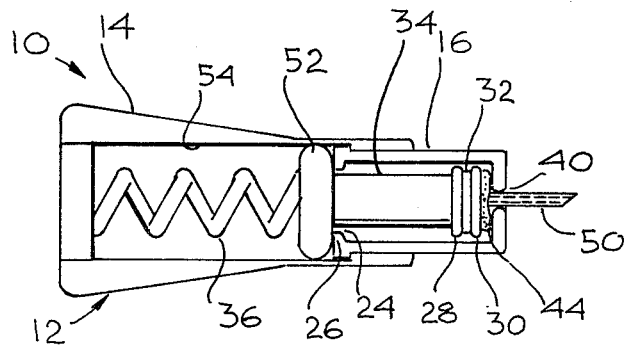
Fig. 2
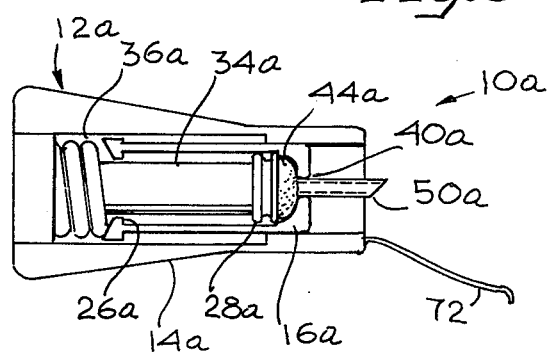
Fig. 6
Fig. 3

ANTI-RAPE DEVICE

BACKGROUND OF THE INVENTION

1. Field of the Invention

The present invention generally relates to rape prevention and more particularly to an improved intravaginal rape-inhibitingdevice.

2. Prior Art

Guns, whistles, aerosol sprays of various types and karate, ju-jitsu and other self-protection techniques are frequently considered for anti-rape purposes. Unfortunately, the numbers of rapes per year are rapidly increasing and convictions are few and far between. Rapes occur despite the described preventive measures because of the greater strength of the male and also because of the element of surprise, generating a paralyzing fear, not only of rape but of death. Rape victims are frequently threatened with deadly weapons during the act of rape so that resistance is futile and sometimes fatal. It is not unknown for the rapist to kill the victim to keep his identity unknown. Few rapists are ever caught at all, much less in the act, so that victims are discouraged from reporting the rape.

There obviously is a great need for a safe, inexpensive but effective device which will help prevent and terminate rapes, will help protect the victim and will result in a larger number of rapists being caught and convicted. Preferably, such device should be one which does not require any overt positive action by the victim which will alert the rapist and which can be countered by the rapist.

SUMMARY OF THE INVENTION

The improved anti-rape device of the present invention satisfies all the foregoing needs. It is small, inexpensive, light and safe and it is totally concealable within the vagina of the wearer. It does not require any positive act by the wearer, once in place, and is triggered to release rape-deterring fluid only when the vagina is penetrated, as by a penis during rape. The rape-deterring fluid is preferably one which can easily, safely and rapidly immobilize the rapist, leaving him at the scene of the crime, with the evidence at hand, to be picked up by the police. Such a device obviously would also discourage future rapes by any rapist who had already encountered it and its effects. The device can be made as light and as easy to insert and withdraw as a tampon and thus can be removed and reinserted at will, while remaining cocked and ready for action. Further features are set forth in the following detailed description and accompanying drawings.

DRAWINGS

FIG. 1 is a schematic side elevation of a first preferred embodiment of the improved anti-rape device of the present invention;

FIG. 2 is a schematic longitudinal cross-section of the device of FIG. 1 shown in the cocked position;

FIG. 3 is a schematic longitudinal cross-section of the device of FIG. 1 shown in the discharged position;

FIG. 4 is a schematic side elevation, partly broken away, of a second preferred embodiment of the improved anti-rape device of the present invention, including an applicator and a withdrawal string;

FIG. 5 is a schematic longitudinal section of the device of FIG. 4, after removal of the applicator, in the cocked position; and, FIG. 6 is a schematic longitudinal section of the device of FIG. 5 shown in the discharged position.

DETAILED DESCRIPTION

FIGS. 1-3

A first preferred embodiment of the improved anti-rape device of the present invention is schematically depicted in FIGS. 1-3. Thus, device 10 is shown which comprises a hollow housing 12 formed of a first, generally flask-shaped or cylindrical chamber 14 within which is slideably received a second tubular chamber 16. Chamber 14 is designed to seat comfortably in the vagina and to hold its position thereof. Obviously, other shapes can be employed. Chamber 16 protrudes forwardly through the open front end 18 of chamber 14. A ring 20 at the outer rear periphery of chamber 16 is engageable with a ledge 22 in chamber 14 adjacent front end 18 to limit the forward movement of chamber 16 relative to chamber 14 and to prevent total disengagement of the two chambers.

Chamber 16 has an open rear end 24 defined by an annular inwardly directed detent 26. A pair of spaced annular rings 28 and 30 define a groove 32 at the front end of an elongated ram 34, within which groove 32 detent 26 is releasably held, ram 34 extending longitudinally of chamber 14, to position ring 20 against ledge 22. Thus, chamber 16 is urged forward, by ram 34, relative to chamber 14, ram 34 being biased forward by a coiled spring 36 positioned within chamber 14 between the rear end 38 thereof and ram 34, as shown in FIG. 2.

Chamber 16 has a central spring opening 40 in the front end 42 thereof. A hypodermic syringe 44 is wholly disposed within chamber 16, when chamber 16 is in the cocked position shown in FIG. 2. Syringe 44 includes a collapsable hollow bulb 46 filled with rape-deterring fluid 48 and connected to a forwardly directed hollow needle 50 aligned with opening 40 and capable of delivering the fluid from bulb 46.

Fluid 48 preferably is a quick-acting safe narcotic such as scopolamine hydrochloride, chloral hydrate, calcium pentobarbital, or the like, in an amount just sufficient to fully anesthetize a rapist. Alternatively, fluid 48 can be a strong instant skin irritant, such as formic acid which produces, when injected, symptoms similar to a bee sting or wasp sting. Hydrochloric acid or another safe skin irritant could also be used as fluid 48. Fluid 48 should be strong enough to cause overpowering results, preferably unconsciousness in the rapist or at least such instant concern for his penis that the rape will terminate instantly and the victim can escape without further harm.

As indicated above, device 10 is designed to be worn longitudinally in the vagina with chamber 16 facing the front of the vagina. Ram 34 has an enlarged alignment ring 52 at the rear end thereof which is dimensioned to ride in the internal bore 54 of chamber 14. Rings 28 and 30 and/or detent are fabricated of materials with sufficient elasticity so that detent 26 can be forced from groove 32. For this purpose, detent 26 and/or rings 28 and 30 can be made of nylon, rubber or the like.

When a penis forcibly penetrates a vagina containing device 10, it first encounters chamber 16 and then drives device 10 back against the cervix, eventually overcoming the holding action of detent 26 in groove 32. That is, it displaces detent 26 rearwardly of ring 28. When this happens, spring 36 suddenly is released to drive ram 34 rapidly forward (FIG. 3) through chamber 16, first shoving syringe 44 forward ahead of it, so as to protrude needle 50 forward through opening 40 and into the rapist's penis and then collapsing bulb 46 so as to shoot fluid 48 into that penis through needle 50 for the desired results. This all happens in a fraction of a second. The rapist will immediately disengage from the victim and either collapse unconscious or suffer sufficient temporary penis pain to direct his whole attention to that organ along, permitting the victim to escape. It is greatly preferred that fluid 48 be a safe narcotic so that the rapist is immediately rendered helpless and the victim can call the police in to arrest him. The evidence of the discharged syring 44 still in the vagina and its contents in the rapist's penis will serve to help obtain a conviction.

Device 10 is thus safe, easy to use and convenient and can be fabricated in any suitable size, shape and configuration of any suitable materials, such as plastic, metal, wood derivatives, etc. Preferably it is of smooth, inexpensive, easily fabricated plastic. Typical dimensions are a maximum diameter of ¾", minimum diameter of 15/32" and length of 1-9/64" for chamber 14, a diameter of 13/32" for and length of ⅝" for chamber 16 and an overall length of 1-⅜" for device 10. Thus, device 10 may be, for example, about the size of a vaginal Tampon. Needle 50 may be any standard fine gauge hypodermic needle, preferably protrudable only about 3/16" into the penis and bulb 46 may contain, for example, 1-10 cc. of injectable fluid 48.

FIGS. 4-6

A second preferred embodiment of the invention is schematically depicted in FIGS. 4-6. Components substantially similar to those of FIGS. 1-3 bear the same numerals but are succeeded by the letter "a". Thus, device 10a is depicted which includes housing 12a, chambers 14a and 16a and suitable insertion and withdrawal components. In this regard, an open ended cylindrical tube 60 is releasably disposed around housing 12a. Tube 60 has a closed, cone-shaped end 62 formed of a folded fluted material such as paper, thin plastic, etc. End 62 is openable to extrude housing 12a therethrough. Disposed within the opposite end 64 of tube 60 is a pusher assembly 66 comprising a bracket 68 dimensioned to releasably engage the front end 18a of chamber 14a without touching chamber 16a, and a push rod 70 connected to bracket 68 and extending out end 64 of tube 60. Lastly, a withdrawal string 72 is connected to end 18a and extends out of end 64.

Tube 60 is first inserted into a vagina, then rod 70 is pushed through tube 60 until housing 12a exits tube 60 through end 62, after which tube 60 is withdrawn, leaving device 10a in place with string 72 extending out the vagina. Tube 60 and bracket 68 preferably are interconnected (not shown) so as to permit movement of bracket 68 only toward end 62 relative to tube 60, whereupon withdrawal of tube 60 can be effected by rod 70 and bracket 68.

Device 10a differs from device 10 only in one other major respect. Ram 34a is stationary, being fixed to end 38a of chamber 14a, and having no ring at the rear end thereof, and spring 36a is connected to rear end 24a of chamber 16a. Thus, in the cocked, releasably locked position shown in FIG. 5, spring 36a is stretched forward, with detent 26a being releasably held in groove 32a between rings 28a and 30a and with ring 20a abutting ledge 22a. When device 10a is fired, due to a rapist's penis shoving chamber 16a rearwardly relative to chamber 14a during the act of rape, thus driving detent 26a rearward of ring 28a, spring 36a is suddenly free to strongly and rapidly pull chamber 16a rearwardly so that syringe 44a is mashed against ram 34a, first extruding needle 50a through opening 40a, then collapsing bulb 46a to inject fluid 48a through needle 50a into the rapist's penis, all within a fraction of a second. Thus, device 10a performs the same rape-deterring and rape-terminating functions as device 10. Device 10a can be made economically and inexpensively from any suitable materials such as those set forth above for device 10.

Various other modifications, changes, alterations and additions can be made in the improved anti-rape device of the present invention. All such modifications, changes, alterations and additions as are within the scope of the appended claims form part of the present invention.

What is claimed is:

1. An improved anti-rape device, said device comprising, in combination:
   a. a hollow housing dimensioned to be releasably received within a human vagina, said housing having a front opening;
   b. a hypodermic syringe containing a volume of rape-deterring fluid and a needle for injection of said fluid, said syringe being disposed in said housing with the front end of said needle facing and aligned with said opening; and,
   c. syringe-actuator means in said housing, said actuator means including
      i. biasing means rearward of said syringe in said housing for biasing said syringe into a needle-protruding, fluid-injecting position,
      ii. cocking means for releasably holding said syringe in a needle-retracted position in said housing, and,
      iii. trigger means for releasing said syringe from said cocking means, to allow said biasing means to effect rapid protrusion of said needle through said opening and injection of said fluid through said needle into the penis of a rapist during penetration of a vagina containing said device.

2. The improved device of claim 1 wherein said device includes means for insertion of said housing into a vagina and for subsequent withdrawal of said housing from said vagina.

3. The improved device of claim 1 wherein said insertion means includes open-ended tube means enclosing said housing and pusher means for urging said housing from said tube means, and wherein said withdrawal means includes string means connected to the front end of said housing and adapted to protrude from a vagina when said device is in place in that vagina.

4. The improved device of claim 1 wherein said housing comprises a first chamber and a second chamber, said second chamber being slideably disposed within and extending forward of said first chamber and including said trigger means, said second chamber containing said front opening, said syringe being disposed within said second chamber, said first chamber containing limit means to prevent total disengagement of said two chambers.

5. The improved device of claim 4 wherein said second chamber has an open rear end defining a detent, wherein said biasing means comprise a spring disposed in said first chamber behind said second chamber, and wherein said cocking means comprises a ram disposed in said first chamber between said spring and second chamber, the front end of said ram bearing holding means releasably engaging said detent and releasably holding said second chamber in a position fully enclosing said syringe, whereby the act of rape penetration of a vagina containing the device will result in the penis forcing movement of said second chamber rearwardly relative to said first chamber, driving said detent past said holding means, thereby allowing said spring to drive said ram and syringe together to force said needle forwardly from said opening and inject said fluid into the penetrating penis.

6. The improved device of claim 5 wherein said holding means comprises a pair of spaced rings disposed around the outer periphery of said ram at the front end thereof and wherein in the locked position said detent is disposed between said rings.

7. The improved device of claim 6 wherein said first and second chambers, rings and detent comprise nylon.

8. The improved device of claim 5 wherein said spring is a compressed spring and wherein upon rearward disengagement of said detent from said holding means, said ram is adapted to be driven forwardly in said second chamber by said spring.

9. The improved device of claim 5 wherein said spring is connected to the rear end of said second chamber whereby, upon rearward disengagement of said detent from said holding means, said spring pulls said second chamber rearwardly relative to said first chamber.

10. The improved device of claim 6 wherein said syringe includes a pouch containing said fluid, which pouch is collapsable by impingement against said ram.

* * * * *